United States Patent
Pazik et al.

(12) 
(10) Patent No.: US 6,814,992 B2
(45) Date of Patent: Nov. 9, 2004

(54) ANAEROBIC FERMENTATION METHOD AND APPARATUS

(76) Inventors: Andre J. Pazik, 853 E. Robinson St., North Tonawanda, NY (US) 14120; Daniel C. Kornacki, 1165 Oliver St., North Tonawanda, NY (US) 14120

( * ) Notice: Subject to any disclaimer, the term of this patent is extended or adjusted under 35 U.S.C. 154(b) by 120 days.

(21) Appl. No.: 10/289,033

(22) Filed: Nov. 6, 2002

(65) Prior Publication Data

US 2004/0086608 A1 May 6, 2004

(51) Int. Cl.⁷ .............................. C12C 13/00; C12G 3/00
(52) U.S. Cl. ..................... 426/231; 73/861.41; 99/276; 99/277; 99/323.1; 426/11; 426/592
(58) Field of Search ............................ 426/231, 11, 15, 426/592; 99/276, 277, 277.1, 278, 323.1; 73/861.41

(56) References Cited

U.S. PATENT DOCUMENTS

| | | | |
|---|---|---|---|
| 2,023,153 A | 12/1935 | Stella | 217/105 |
| 2,594,668 A | 4/1952 | Mannal | 73/194 |
| 2,683,986 A | 7/1954 | Bartlett et al. | 73/194 |
| 2,967,450 A | 1/1961 | Shields et al. | 88/14 |
| 3,681,985 A | 8/1972 | Rudd | 73/194 E |
| 4,517,884 A | 5/1985 | Jandrich | 99/276 |
| 4,557,186 A | * 12/1985 | Brown | 99/278 |
| 4,717,031 A | 1/1988 | Hewson | 215/1 C |
| 4,842,869 A | 6/1989 | Forino | 426/8 |
| 5,092,181 A | 3/1992 | Kuss et al. | 73/861.41 |
| 5,555,797 A | 9/1996 | Chun | 99/468 |
| 5,950,524 A | 9/1999 | Reitz et al. | 99/277.1 |

FOREIGN PATENT DOCUMENTS

| | | |
|---|---|---|
| DE | 412 918 | 5/1925 |
| DE | 957 563 | 2/1957 |
| FR | 2 801 676 | 1/2001 |

\* cited by examiner

*Primary Examiner*—George C. Yeung
(74) *Attorney, Agent, or Firm*—Simpson & Simpson, PLLC (57) ABSTRACT

A method and apparatus for monitoring a liquid undergoing anaerobic fermentation in a vessel is disclosed. The apparatus comprises an airlock containing a fluid for sealing the vessel and an electrical circuit operatively arranged to pass a current through the fluid to detect passage of bubbles through the airlock.

23 Claims, 7 Drawing Sheets

ANAEROBIC FERMENTATION METHOD AND APPARATUS

REFERENCE TO COMPUTER PROGRAM LISTING APPENDIX

This patent includes a computer program listing appendix on compact disc. Two duplicate compact discs are provided herewith. Each compact disc contains a computer program listing as follows:

Filename: hc11

Size: 4 kilobytes

Date Created: Oct. 15, 2002

Filename: switch28

Size: 14 kilobytes

Date Created: Oct. 15, 2002

The computer program listing appendix is hereby expressly incorporated by reference in the present application.

TECHNICAL FIELD

The present invention relates generally to a method and apparatus useful during anaerobic fermentation, and more particularly to a method and apparatus for measuring the volume and rate of gas produced during anaerobic fermentation, this invention having particular utility during the making of alcoholic beverages.

BACKGROUND OF THE INVENTION

Figure 1:
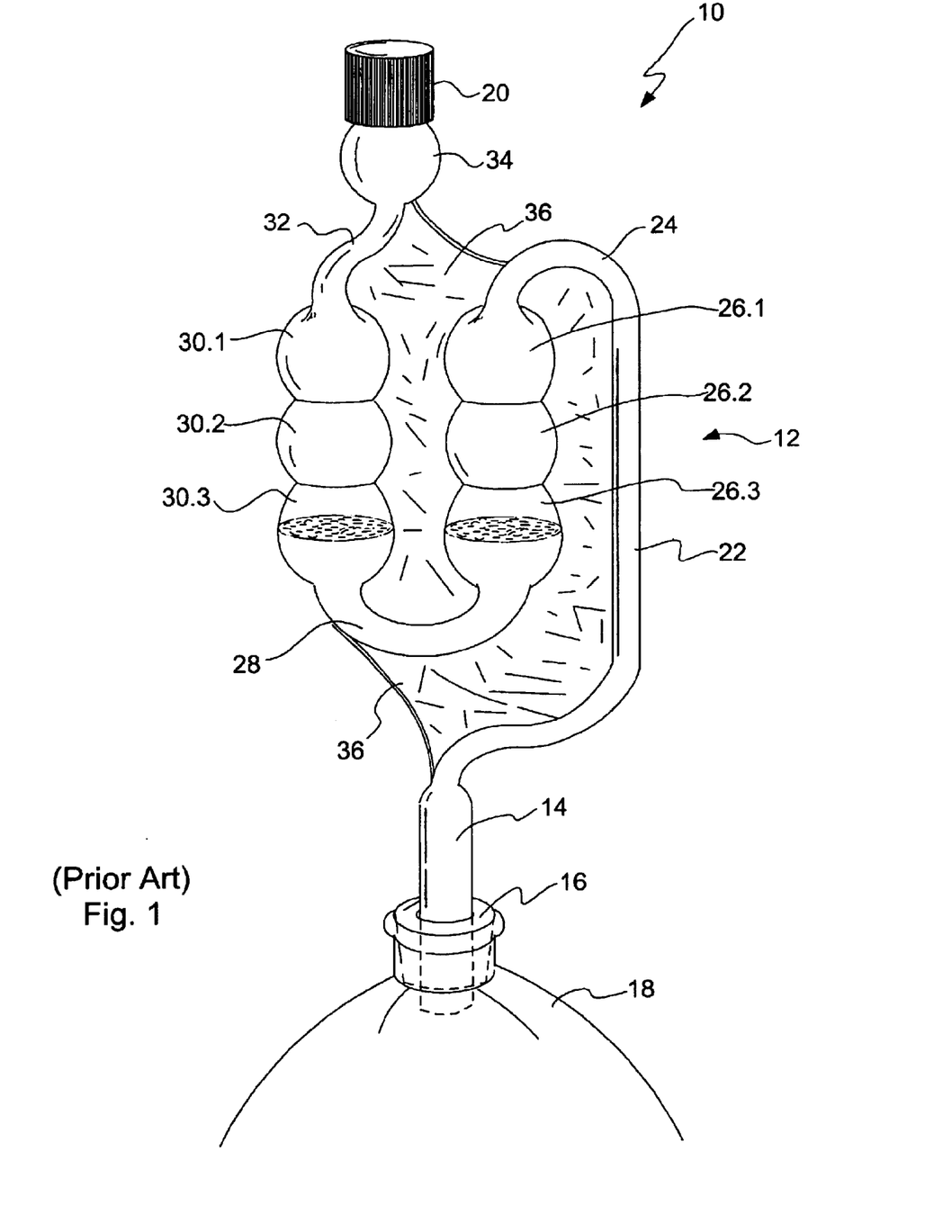
FIG. 1 illustrates a prior art "S" type airlock sold under the tradename of TRIPLE RIPPLE.

It is common when making alcoholic beverages in the home to place the liquid subject to fermentation into a vessel for anaerobic fermentation, the vessel being closed by a fermentation airlock. The purpose of the fermentation airlock is to prevent undesirable dust and bacteria from contaminating the material being fermented. Therefore it is common to utilize an airtrap, the gas produced by fermentation bubbling though a liquid in the airtrap, the liquid typically containing water and a sterilizing agent such as sodium or potassium metabisulfite. Differing types of fermentation locks are employed, various examples being shown in U.S. Pat. Nos. 4,517,884, 4,842,869, and 5,950,524. A favorite form of airlock is the "S" type airlock, variations being shown in U.S. Pat. Nos. 2,023,153 and 4,717,031, and German patents 412,918 and 957,563. Another prior art form of "S" type airlock is shown in FIG. 1 of this application, this particular form of "S" type airlock being sold under the tradename of TRIPLE RIPPLE.

The TRIPLE RIPPLE airlock is molded from a clear plastic, all airlocks being quite uniform in size. It has been observed that when using a TRIPLE RIPPLE airlock that each bubble has substantially the same volume, i.e., 1.7 ml. It is also known that during fermentation that equal mole volumes of $CO_2$ and alcohol are produced.

OBJECTS AND SUMMARY OF THE INVENTION

It is an object of the present invention to monitor bubble events through an "S" type airlock to determine the volume and rate of alcohol production. A bubble event, as used in this application, refers to when a bubble passes through the air lock.

More particularly, it is a further object of the present invention to utilize the bubble events to set various alarms so that the operator of the anaerobic fermentation apparatus will be provided with certain information to facilitate the making of alcoholic beverages.

The above objects, and other objects and advantages of this invention will become more apparent to those skilled in the art after a consideration of the following detailed description taken in conjunction with the accompanying drawings in which a preferred form of this invention is illustrated.

BRIEF DESCRIPTION OF THE DRAWINGS

It should be appreciated that, in the detailed description of the invention which follows, like reference numbers on different drawing views are intended to identify identical structural elements of the invention in the respective views.

DETAILED DESCRIPTION

With reference initially to FIG. 1, a TRIPLE RIPPLE airlock is illustrated, the TRIPLE RIPPLE airlock being indicated generally at 10. This airlock consists of a molded clear plastic member indicated generally at 12, the plastic member including an "S" shaped passageway which will be described later. Extending downwardly from the "S" shaped passageway is a mounting stem 14 which is inserted into the rubber bung or cork 16 of a fermenting vessel 18 so as to be an airtight fit. The airlock is provided with a dust cap 20 at its upper end.

The "S" shaped passageway includes an upwardly extending portion 22 which is in direct communication with the stem 14, the portion 22 being essentially cylindrical in cross section. A "U" shaped member 24 having a circular cross section connects the portion 22 with a downwardly extending portion 26 having upper, intermediate, and lower bulbs 26.1, 26.2, and 26.3, respectively. A further "U" shaped member 28 having a circular cross section connects the lower end of the downwardly extending portion 26 with an upwardly extending portion 30 provided with upper, intermediate and lower bulbs 30.1, 30.2, and 30.3, respectively. An upwardly extending member 32 is provided with a bulb 34 at its top end, which bulb receives the dust cap 20. A clear plastic web or flashing 36 extends between the downwardly extending portion 26 and the upwardly extending portion 30, and also between the downwardly extending portion 26 and the upwardly extending portion 22 to keep the various parts in fixed relationship to each other.

After the liquid to be fermented is placed in the vessel, which liquid may be a wine must, the vessel is sealed with an airlock at the commencement of anaerobic fermentation. To this end, a sterilizing liquid is placed in the "S" shaped airlock, the sterilizing liquid filling the "U" shaped member 28 and ½ of each of the lower bulbs 26.3 and 30.3, the sterilizing liquid being indicated generally at SL in FIG. 2. The sterilizing liquid typically contains either sodium or potassium metabisulfite, although other sterilizing agents may be used. During anaerobic fermentation the yeast is less active than during the initial aerobic fermentation, and the $CO_2$ produced will escape through the sterilizing liquid one bubble at a time.

Figures 2, 3:
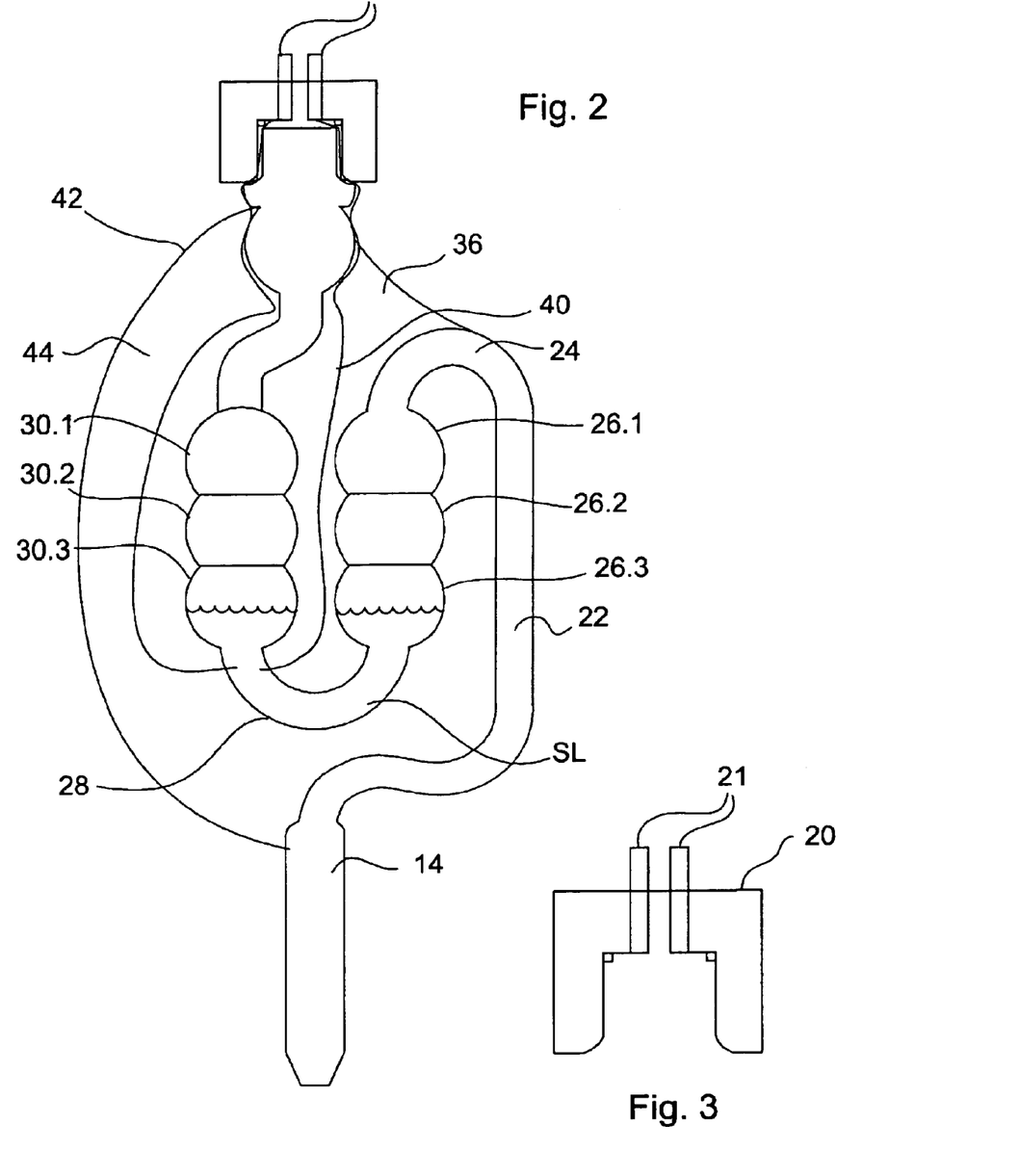
FIG. 2 illustrates how a prior art "S" type airlock may be modified to identify bubble events, the airlock being provided with electrodes.
FIG. 3 shows a dust cap for the modified "S" type airlock, which dust cap is provided with suitable contacts for contacting the electrodes in the modified "S" type airlock.

With reference to FIG. 2, it can be seen that the "S" type airlock of the present invention is provided with two electrodes 40, 42. Electrode 40 is embedded in the flashing 36 which extends between the downwardly extending portion 26 and the upwardly extending portion 30. Additional flashing 44 is provided to one side of the upwardly extending portion 30 for the receipt of electrode 42. As can be seen from FIG. 2, the electrodes have lower terminal ends that extend into the passageway 28. Normally the ends of the electrodes are covered with the sterilizing liquid, which conducts electricity. Thus, when a voltage is applied between them, current flows between the electrodes. However, when a bubble passes through the tube 28, the current flow between the electrodes is interrupted. Dust cap 20, shown in FIG. 3, prevents dust from settling into the airlock when it is engaged with the top of airlock 12. Conducting members 21 connect to electrodes 40 and 42.

Figure 4:
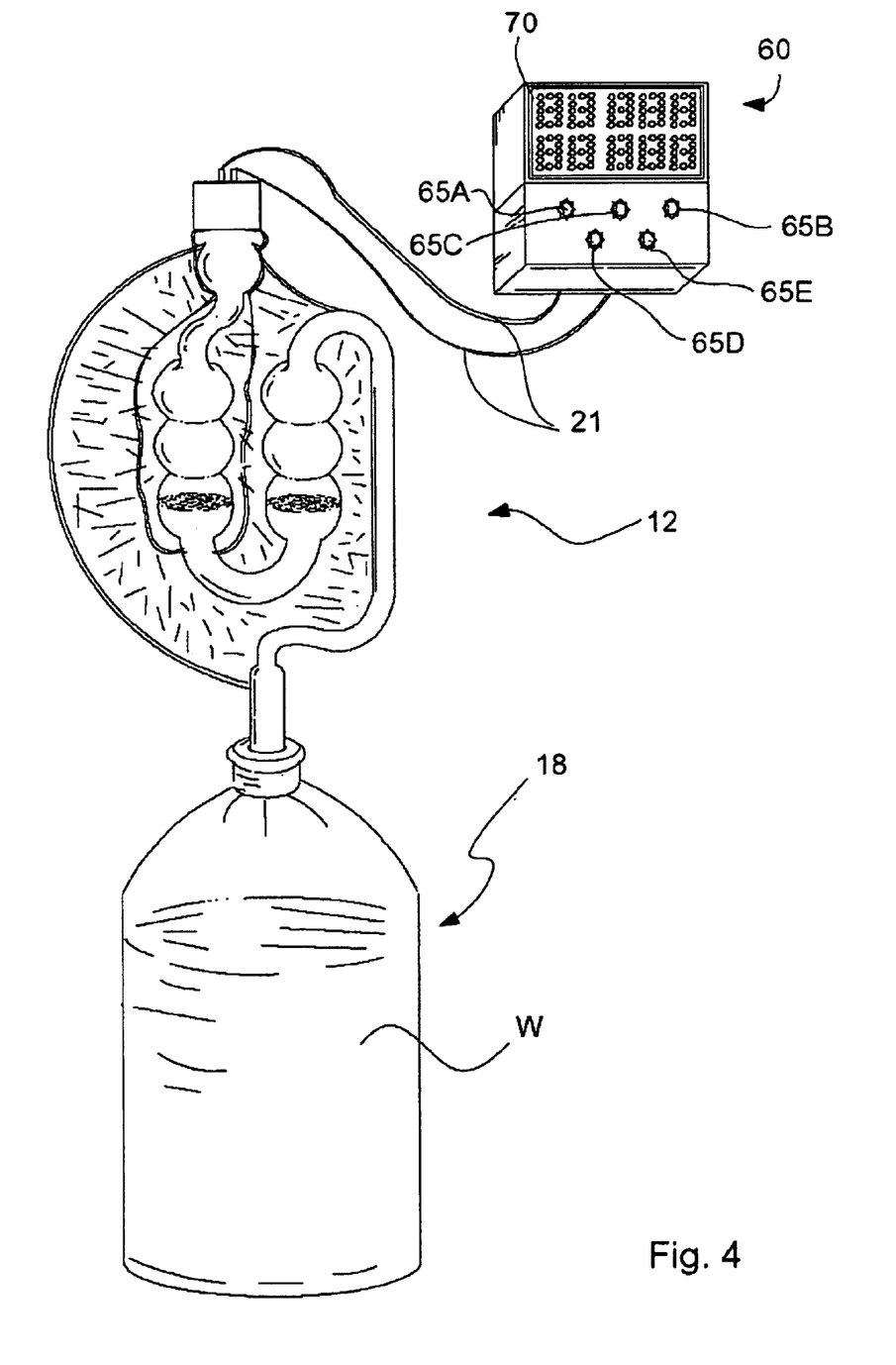
FIG. 4 shows the modified prior art airlock in combination with an electronic monitoring and alarm device, the airlock being mounted on a vessel suitable for anaerobic fermentation.

As illustrated in FIG. 4, electrodes 40 and 42 are connected to control means 60 through conducting members 21. Control means 60 comprises control buttons 65A, 65B, 65C, 65D, and 65E, and a display 70. Bottle 18 contains wine must W. Control means 60 counts the number of times the current between electrodes 40 and 42 is interrupted. Control means 60 determines the status of the fermenting liquid based on the history of bubbles detected. Control means 60 displays the status of the fermenting liquid on display 70.

Figure 5:
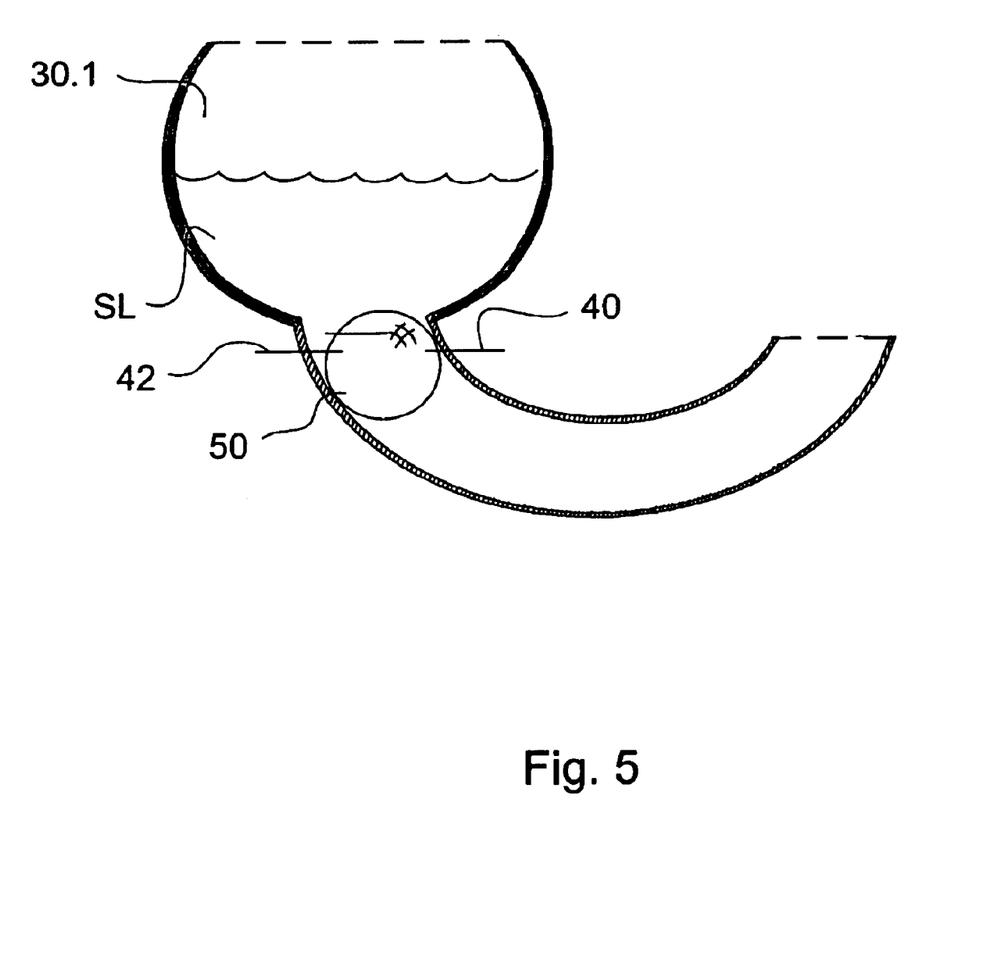
FIG. 5 shows a bubble interrupting the flow of current through between the electrodes, signaling a bubble event.

The interruption of the current between the electrodes is illustrated in FIG. 5. Bubble 50, created by the production of $CO_2$ during fermentation, envelops the exposed conductive material of both electrodes. Thus, with a low voltage drop across the electrodes, the gas does not conduct electricity between the electrodes. A preferred voltage drop across the electrodes is approximately 5 V, although other voltage drops might be suitable. The control means of the apparatus records each interruption in the current as a bubble event.

Figure 6:
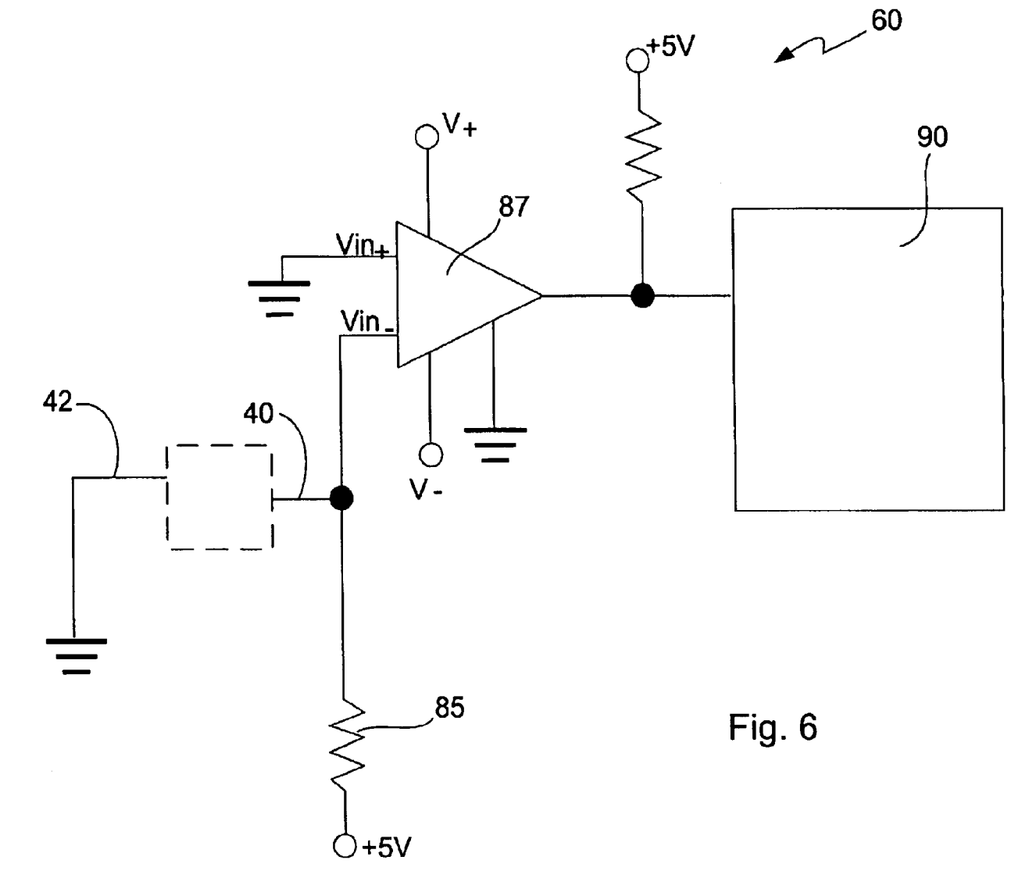
FIG. 6 shows an embodiment of the electrical circuit of the control means.

FIG. 6 is a schematic of an embodiment of the electrical circuit of the control means. The circuit shown comprises electrodes 40 and 42, a 5 V source, resistor 85, operational amplifier (op amp) 87, positive and negative power supplies $V_+$ and $V_-$ to power the op amp, and processor 90. Processor 90 is a conventional microprocessor, well known to those in the electronics art. The 5 V source is connected across electrodes 40 and 42 through resistor 85. When current exists between the electrodes, $V_{in-}$ is 0 V. (The 5 V source is shorted to ground.) However, when a bubble interrupts the current through the electrodes, $V_{in-}$ is no longer zero. (Ground is separated from $V_{in-}$ by an open circuit.) $V_{in+}$ is connected to ground. Thus processor 90 can determine the presence of a bubble between electrodes 40 and 42 from the output of operational amplifier 87.

Figure 7:
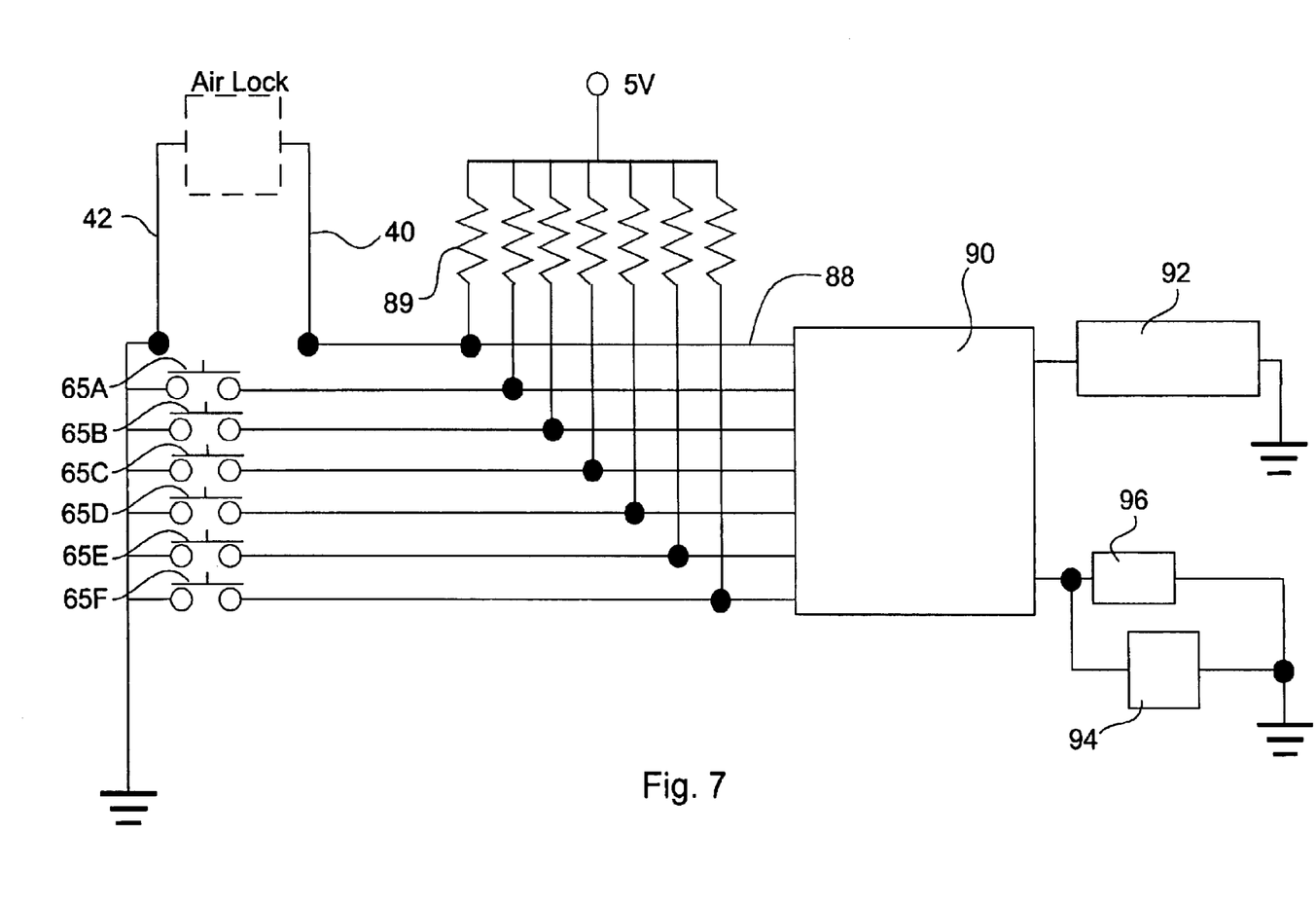
FIG. 7 shows an alternate embodiment of the electrical circuit of the control means.

FIG. 7 shows a second possible embodiment of control means 60. This embodiment comprises a plurality of control buttons 65A, 65B, 65C, 65D, 65E, and 65F, electrodes 40 and 42, a 5 V source, resistor 89, pin 88 of processor 90, audio alarm 92, and visual alarm 94. Pin 88 of processor 90 is connected to electrode 40 and to a 5 V source through resistor 89. Electrode 42 is connected to ground. When current exists between the electrodes, pin 88 is shorted to ground. When the current is interrupted by a bubble, pin 88 will be lifted to a non-zero voltage. (The voltage level will depend on the resistance value of resistor 89). In this manner, processor 90 can determine the presence of bubbles between electrodes 40 and 42.

To use the above-described device, a measure volume of a liquid subject to fermentation, such as a wine-must, is placed in a container. (This is typically done after a period of aerobic fermentation and a hydrometer measurement to determine the proportion of sugar remaining.) The airlock of the present invention is inserted in the neck of the container. The user programs the volume of liquid present in the container using the control buttons.

In a preferred embodiment, control means 60 are configured as follows. First, the batch size must be set. Button 65A increases the batch size by 10 liters each time it is pushed. Button 65B increases the batch size one liter each time it is pushed. Button 65C accepts the batch size when it is pushed, if the batch size is non-zero. (Buttons 65D and 65E have no function in setup mode). After the batch size is set, the user can enter a user specified time alarm, to be activated when the enter amount of time passes without a bubble being detected. Button 65A increases this alarm time by one hour each time it is pushed. Button 65B increases this alarm time by one minute each time it is pushed. Button 65C accepts the current alarm time. (Zero may be entered if no user specified time alarm is desired.) When the user specified alarm is set, the user can then enter an alcohol alarm level. Button 65A increases the alcohol level alarm by one percent each time it is pushed. Button 65B increases the alcohol level alarm by one tenth of one percent each time it is pushed. Button 65C accepts the current alcohol level. After the alcohol level alarm is set, the user can activate the 24 hour alarm. Button 65A enables the 24 hour alarm. Button B disables the 24 hour alarm. Button 65C accepts the current 24 hour alarm status. The control means then detects the bubbles of gas escaping from the airlock and displays the status of the liquid on display 70.

The status is determined based on the history of bubbles detected by control means 60. In one embodiment, airlock 12 is configured such that the escaping bubbles have a volume at room temperature and 1 atmosphere of pressure of 1.7 ml. (It is assumed that the fermentation is done at a constant temperature, thus an equal amount of gas is contained in each bubble). Thus, by counting the number of bubbles, control means 60 can determine the amount of gas to escape from the airlock. According to calculations known in the art, the amount of alcohol generated during anaerobic fermentation can be determined based on the volume of $CO_2$ generated (assuming substantially all of the escaping gas is $CO_2$ generated by fermentation) and the amount of liquid present in the container (input using the control buttons, as discussed above). Accordingly, control means 60 can calculate the volume of alcohol generated and display this amount on display 70.

In a preferred embodiment the buttons of the control means function as follows. Button 65A scrolls the display of the bubble events towards the most current event. Button 65B scrolls the display of the bubble events towards the least recent event. Button 65C deletes the display of the displayed event if pressed alone. Button 65D caused the control means to reenter setup mode. Button 65E silences current alarms and calls up a screen to review past alarms. Display 70 is set to the most recent event when button 65E is released. When buttons 65C and 65E are pressed simultaneously, past alarms are cleared.

As discussed above, a user can preprogram a percentage of alcohol desired with the control buttons. In this case, control means 60 displays a countdown of the amount of alcohol still to be generated. Control means 60 can include an audible alarm 94 and/or visual alarm 96 to signal a user when the desired amount of alcohol has been produced. This can be especially useful in making beverages wherein some fermentation is desired after the liquid is bottled. The alarm can be set to alert the user when a portion of the desired alcohol has been produced. The user can then transfer the beverage to individual bottles for the remaining fermentation. This is also useful for the production of a sweet beverage. The user can stop fermentation before all the sugar has been consumed by the yeast.

Control means 60 also includes timing means to determine the amount of time between each bubble. Counting means displays the amount of time since the last bubble on display 70. Audible and/or visible alarms can be activated to alert the user after a specified time without a bubble has been reached. In one embodiment, this time period is 24 hours. In another embodiment, this time period is set by the user using the control buttons (the user specified alarm discussed above).

A potential problem with fermentations that can take a long period of time is the evaporation of the sterilizing liquid. If the sterilizing liquid evaporated to the point wherein outside air may pass into vessel 18, then the fermentation may be spoiled. The present invention warns a user when the level of the sterilizing liquid is low. Electrodes 40 and 42 are placed in member 28 such that they are exposed to air before the liquid level drops to an extent that air could reenter vessel 18, as shown in FIG. 2. Control means 60 times the length of the bubbles. If the sterilizing liquid has partially evaporated, then the electrodes will be exposed to air continuously. Thus, when control means 60 detects an interruption of the current that lasts an extended period of time (in one embodiment 1 hour), it displays a low liquid level warning on display 60. Audible and/or visible alarms may also be activated. In addition, bubble detection indicator 92 is lit when a bubble is being detected (when current is not flowing between electrodes 40 and 42.) This can also allow a user to determine there is a problem if the bubble detection indicator remains lit for an extended period of time. The low liquid level warning and bubble detection indicator allow a user to replace the lost sterilizing liquid before the fermenting liquid is spoiled.

Figure 8:
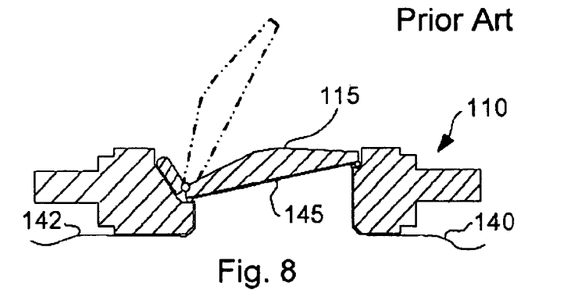
FIGS. 8 through 10 show valves known in the art.
Figure 9:
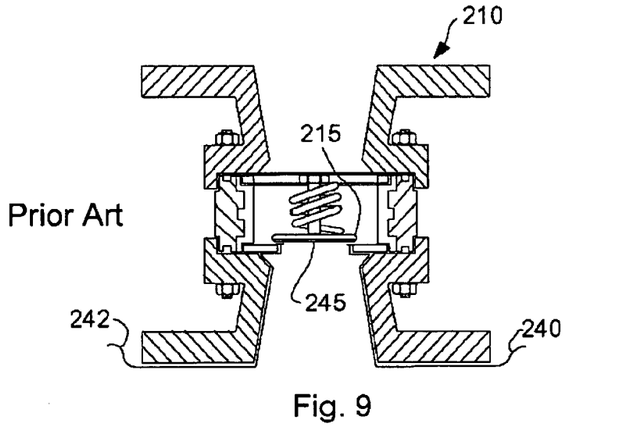
Figure 10:
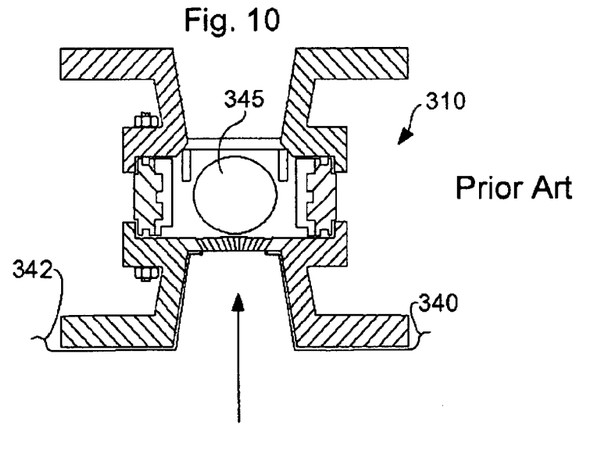

FIGS. 2, 4, and 5 show the present invention being practiced with an "S" type airlock. However, it should be readily apparent to one skilled in the art that other airlocks or valves may be modified to practice the present invention. FIGS. 8–10 illustrate several valves known in the art. FIG. 8 shows a flapper check valve 110. Electrodes 140 and 142 contact conducting strip 145 on flapper 115 when the valve is closed. Thus, when the valve is closed, current flows from electrode 140 to electrode 142 through strip 145. When flapper 115 is forced open by gas pressure, the current flowing between electrode 140 and electrode 142 is interrupted. Thus, the number of times gas escapes from the valve can be counted. The amount of gas that escapes each time is measured and programmed into control means 60. In this manner, a fermentation process can be monitored as described above. In a similar manner, FIG. 9 shows a piston check valve 210 comprising electrodes 240 and 242, and valve member 215 having conducting strip 245 on a surface thereon. When the valve is closed, current flows from electrode 240 to electrode 242 through strip 245. When member 215 is forced open by gas pressure, the current flowing between electrode 240 and electrode 242 is interrupted. FIG. 10 shows ball check valve 310 comprising electrodes 340 and 342 and conducting ball 345. When the valve is closed, current flows from electrode 340 to electrode 342 through conducting ball 345. When ball 345 is forced up by gas pressure, the current flowing between electrode 340 and electrode 342 is interrupted. The amount of gas released each time the valve opens is used to determine how much gas is produced during fermentation, in the manner described above. These modifications, including the use of the practicing of the present invention with other valves not shown, is intended to be within the spirit and scope of the invention as claimed. In the present specification and claims, the word "airlock" is intended to mean any airlock or valve known in the art or hereafter developed that can be modified as described herein to practice the present invention.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A method for determining an amount of alcohol produced during anaerobic fermentation in a sealed anaerobic fermentation vessel containing a liquid being fermented, said vessel sealed with an airlock, the method comprising the steps of:

counting bubbles which pass through said airlock to determine a volume of gas produced; and, determining said amount of alcohol produced based on said volume of gas produced.

2. The method recited in claim 1 further including the step of determining the rate of fermentation by determining the interval between bubbles.

3. The method recited in claim 1 further including the step of activating an alarm when a desired amount of alcohol is produced.

4. The method recited in claim 1 wherein said airlock is an S-type airlock.

5. The method recited in claim 1 wherein said airlock is a valve.

6. The method recited in claim 5 wherein said valve is a flapper check valve.

7. The method recited in claim 5 wherein said valve is a piston check valve.

8. The method recited in claim 5 wherein said valve is a ball check valve.

9. A method for measuring gas produced during anaerobic fermentation comprising the steps of:

providing a vessel suitable for anaerobic fermentation;

placing liquid materials subject to anaerobic fermentation within the vessel;

sealing the vessel with an S-type airlock; and counting the bubbles which pass through the airlock to determine the volume of gas produced, which volume of gas is proportional to the volume of alcohol produced.

10. The method recited in claim 9 further comprising the step of determining the rate of fermentation by determining the interval between bubbles.

11. An apparatus for monitoring a liquid undergoing anaerobic fermentation in a vessel, comprising:

an airlock containing a fluid for sealing the vessel; and, an electrical circuit operatively arranged to pass a current through said fluid to detect passage of bubbles through said airlock.

12. The apparatus recited in claim 11 wherein said airlock is an S-type airlock.

13. The apparatus recited in claim 11 wherein said airlock is a valve.

14. The apparatus recited in claim 13 wherein said valve is a flapper check valve.

15. The apparatus recited in claim 13 wherein said valve is a piston check valve.

16. The apparatus recited in claim 13 wherein said valve is a ball check valve.

17. The apparatus recited in claim 11 further comprising means for determining the volume of gas produced based on said detected passage of bubbles.

18. The apparatus recited in claim 17 further comprising:

means to determine an amount of alcohol produced based on said amount of gas produced; and, a display operatively arranged to display said amount of alcohol produced.

19. The apparatus recited in claim 18 further comprising:

an alarm operatively arranged to warn a user when a preprogrammed amount of alcohol has been produced.

20. The apparatus recited in claim 11 further comprising:

means for determining the time between bubble detections; and, means for determining the rate of gas production based on said time between bubble detections.

21. The apparatus recited in claim 20 further comprising:

an alarm operatively arranged to warn a user when no bubbles are detected for a predetermined amount of time.

22. The apparatus recited in claim 21 wherein said alarm is operatively arranged to warn a user when no bubbles are detected for 24 hours.

23. The apparatus recited in claim 11 wherein said airlock further comprises a liquid present in said airlock; and, the apparatus further comprising:

means for determining the length of time a bubble is proximate said electrodes; and, an alarm operatively arranged to warn a user when the liquid in said airlock is low, based on said length of time said bubble is proximate said electrodes.

* * * * *

UNITED STATES PATENT AND TRADEMARK OFFICE
CERTIFICATE OF CORRECTION

PATENT NO. : 6,814,992 B2 Page 1 of 1
APPLICATION NO. : 10/289033
DATED : November 9, 2004
INVENTOR(S) : Andre J. Pazik and Daniel C. Kornacki It is certified that error appears in the above-identified patent and that said Letters Patent is hereby corrected as shown below:

On title page insert
(\*) Notice: Subject to any disclaimer, the term of this patent is extended or adjusted under 35 U.S.C. 154(b) by 121 days.

Signed and Sealed this

Twenty-sixth Day of February, 2008

JON W. DUDAS
*Director of the United States Patent and Trademark Office*